United States Patent

Sleigh et al.

[11] Patent Number: 4,894,369
[45] Date of Patent: Jan. 16, 1990

[54] NOVEL 2β-MORPHOLINO-ANDROSTANE DERIVATIVES

[75] Inventors: Thomas Sleigh, Wishaw; David S. Savage, New Mearns; Ian C. Carlyle, Hamilton, all of Scotland

[73] Assignee: Akzo N.V., Arnhem, Netherlands

[21] Appl. No.: 181,139

[22] Filed: Apr. 13, 1988

[30] Foreign Application Priority Data

Apr. 14, 1987 [GB] United Kingdom ............... 8708886

[51] Int. Cl.$^4$ .................... A61K 31/58; C07J 71/00; C07J 43/00
[52] U.S. Cl. .................... 514/176; 540/76; 540/96
[58] Field of Search .................... 540/76, 96; 514/176

[56] References Cited

U.S. PATENT DOCUMENTS 3,553,212  1/1971  Hewett et al. .................... 540/76
3,872,091  3/1975  Hewett et al. .................... 540/96
4,447,425  5/1984  Carlyle et al. .................... 540/96

Primary Examiner—Joseph A. Lipovsky
Attorney, Agent, or Firm—William M. Blackstone

[57] ABSTRACT

Compounds having the formula:

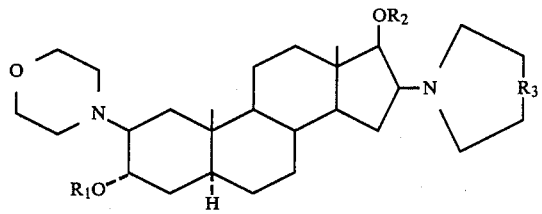

wherein $R_1$ is H or an optionally substituted acyl group having 1–12 carbon atoms,
$R_2$ is H or an acyl group having 1–12 carbon atoms and
$R_3$ is C, N—$CH_3$ or a direct bond;

and mono- or bisquaternary ammonium compounds thereof and acid addition salts of the non- or mono-quaternary ammonium compounds. Process for the preparation of these compounds. Compositions comprising at least one of the above compounds as the active ingredient. The compounds are favorable neuromuscular blocking agents.

6 Claims, No Drawings

NOVEL 2β-MORPHOLINO-ANDROSTANE DERIVATIVES

The present invention is concerned with novel 2β-morpholino-androstane derivatives, with processes for their preparation and with compositions comprising such derivatives as the active ingredient.

2β-morpholino-androstane derivatives have been disclosed in British Pat. No. 1,138,605. These 2β,16β-dimorpholino-androstane derivatives, which are neuromuscular blocking agents, exhibit a low potency.

Surprisingly a novel class of 2β-morpholinoandrostane derivatives has been found with an unexpectedly high potency. Further, these compounds exhibit a very fast onset, have fast recovery characteristics and a favourable specificity of action at nicotinic receptors of the neuromuscular junction compared to muscarinic receptors in the heart. Still further, some of the compounds according to the present invention appeared to be stable in solution; this makes these compounds suitable for ready-for-use preparations.

Accordingly, the present invention is concerned with compounds having the formula:

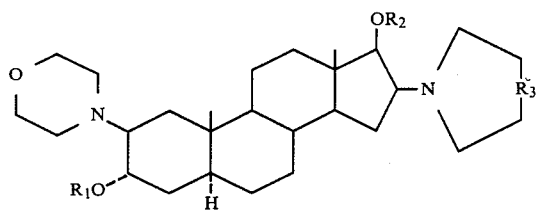

wherein $R_1$ is H or an optionally substituted acyl group having 1–12 carbon atoms;

$R_2$ is H or an acyl group having 1–12 carbon atoms, and $R_3$ is C, N—CH$_3$ or a direct bond;

and mono- or bisquaternary ammonium compounds thereof and acid addition salts of the non- or mono-quaternary ammonium compounds.

$R_1$ in the above formula may be H or an optionally substituted acyl group having 1–12 carbon atoms. Suitable acyl groups are formyl, acetyl, propionyl, butyryl, isobutyryl, valeryl, pivaloyl, 2-carboxyethanoyl, cyclohexanecarbonyl, glycoloyl, trimethylacetyl, phenylpropionyl, propenoyl, 3-butenoyl, 4-pentenoyl, 3-hydroxy-propionyl and 4-hydroxy-butyryl. If $R_1$ is an acyl group preference is given to saturated acyl groups having 1–6 carbon atoms which may be substituted by a carboxy and/or a hydroxy group. The most preferred group for $R_1$ is H.

$R_2$ in the above formula may be H or an acyl group having 1–12 carbon atoms. Suitable acyl groups are the unsubstituted acyl groups mentioned above. Preferably $R_2$ is a saturated acyl group having 1–6 carbon atoms.

$R_3$ in the above formula may be C, N—CH$_3$ or a direct bond. This means that the compounds according to the present invention have a piperidino, a pyrrolidino or a 4'-methyl-piperazino group at position 16β. Preferably this group is piperidino or pyrrolidino.

The quaternary ammonium salts of the compounds according to the above formula also form part of the compounds according to the present invention, as do the acid addition salts of the non- and mono-quaternary ammonium compounds.

The quaternary ammonium compounds may be 2β-quaternary-, 16β-quaternary- or 2β,16β-bis-quaternary ammonium compounds if the group at 16β is piperidino or pyrrolidino; or, in case the group at 16β is 4'-methyl-piperazino, 2β,4'-bis-quaternary or 4'-mono-quaternary compounds.

Preference is given to the 16β-mono-quaternary ammonium compounds having a piperidino or pyrrolidino group at position 16β. A special preference is given to those 16β-mono-quaternary ammonium compounds which have a 3α-OH group, since these compounds are stable in solution.

The quaternising group in the quaternary ammonium derivatives is an aliphatic hydrocarbon group having 1–6 carbon atoms, such as methyl, ethyl, ethynyl, propyl, allyl, propargyl, butyl, isobutyl, pentyl, cyclopropyl, cyclopropylmethyl and cyclohexyl. The anion in the quaternary ammonium derivatives may in principle be any pharmaceutically acceptable organic or inorganic anion, such as methylsulphonate, p-toluene sulphonate, Cl$^-$, Br$^-$ or I$^-$, and is preferably Br$^-$.

The non-quaternised and mono-quaternised compounds may be converted into the acid addition salt thereof, derived from any pharmaceutically acceptable organic or inorganic acid, such as hydrochloric acid, hydrobromic acid, hydro-iodic acid, nitric acid, sulphuric acid, phosphoric acid, acetic acid, propionic acid, butyric acid, caproic acid, malonic acid, succinic acid, glutaric acid, maleic acid, fumaric acid, tartaric acid, malic acid, pyruvic acid, lactic acid and citric acid.

The compounds according to the invention can be prepared by methods employing steps known or obvious to those skilled in the art.

The process for the preparation of the compounds according to claim 1 is characterized in that a compound having the formula:

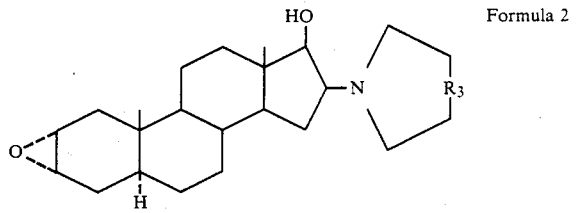

Formula 2

Wherein $R_3$ has the same meaning as already indicated, is reacted with morpholine, that subsequently, if desired, the compound obtained is acylated and/or quaternised by methods obvious to those skilled in the art and that the non- and mono-quaternary ammonium compounds obtained are converted, if desired, into the acid addition salts thereof.

Compounds according to the present invention may be prepared by reacting a compound having the above formula 2 with morpholine.

This reaction is carried out at an elevated temperature, usually between 70° and 250° C., if necessary under pressure and in the presence of water. The reaction tie generally will be between 1 and 5 days. The compounds obtained by conducting this reaction are compounds according to the present invention with $R_1$ and $R_2$ both being H, which compounds may be acylated ($R_1$ and/or $R_2$ being an acyl group as discussed above).

The acylation reactions are carried out by reaction with an acyl halide at a temperature of 5°–60° C. and preferably at room temperature in an organic solvent, like dichloromethane, for 5-48 hours, preferably for 10-30 hours. If acylation of the 17β-OH group is desired only, the amount of acylhalide to be used should be more or less equimolar. If the acylation of both the 17β-OH and the 3α-OH group is desired a molar excess of at least 3:1 of the acyl halide is required.

If only the 3α-OH group should be acylated the steroid is reacted with an acyl halide in a molar excess of at least 3:1 (acyl halide:steroid) and subsequently with an alcohol, like methanol, in order to remove the acyl group from the 17β-OH group. After this reaction step with methanol another acyl group may be incorporated at the 17β-OH group in order to prepare compounds according to the present invention having different acyl groups $R_1$ and $R_2$.

Another way to produce compounds having different acyl groups $R_1$ and $R_2$ is reacting the non-acylated steroid in equimolar amount with an acyl halide and subsequently with an acid anhydride, like succinic anhydride.

The quaternary ammonium compounds are obtained by allowing the 2β-morpholino,16β-pyrrolidino/-piperidino/4'-methyl-piperazino compounds to react with an excess of an aliphatic hydrocarbon halide having 1-6 carbon atoms in a suitable solvent, such as methylene chloride, for several days at room temperature or for several hours at elevated temperature.

The mono-quaternary compounds can be obtained by reacting the 2β-morpholino,16β-pyrrolidino/-piperidino/4'-methyl-piperazino compounds with a restricted amount of hydrocarbon halide while reducing the reaction time, and separating the 2β-mono-quaternary and/or the 16β-mono-quaternary/4'-mono-quaternary compound from the reaction mixture, e.g. by chromatography or by fractional crystallisation. Also use can be made of the fact that the 16β-mono-quaternary compound is sparingly soluble in certain solvents, e.g. ether. The reaction can then be performed in the presence of such solvent so that the 16β-mono-quaternary compound precipitates during the reaction or after the reaction the 16β-mono-quaternary compound is precipitated from the reaction mixture by the addition of such solvent. The 2β-mono-quaternary compound can be obtained from the mother liquor by e.g. chromatography on alumina.

The non-quaternary and mono-quaternary compounds can be converted into the acid addition salts thereof in the usual way by reaction with a pharmaceutically acceptable organic or inorganic acid e.g. in aqueous solution.

The present invention further relates to compositions comprising at least one of the compounds according to the present invention as the active ingredient. Apart from the compounds according to the present invention such compositions comprise the usual ingredients for compositions having neuromuscular activity. Such compositions are made by methods known in the art.

The present compounds are intended particularly for use in clinical practice to produce skeletal muscular paralysis during surgical operations.

The compounds are usually administered by intravenous injection, in initial dosages between 5 and 50 mg (bolus injection), followed if necessary by smaller supplementary dosages.

The present invention is further illustrated by way of the following examples.

EXAMPLE 1

(2α,3α,5α,16β,17β)-2,3-epoxy-16-(1-pyrrolidinyl)-androstan-17-ol

Sodium hydroxide solution (150 ml; 4N) was added to a suspension of (2α,3α,5α,16β,17α)-2,3,16,17-bisepoxy-androstan-17-ol acetate (150 g) in methanol (1.5 l) and the mixture was heated under reflux for 30 min. When the solution had cooled to approx. 40° C., pyrrolidine (225 ml) was added and the solution was heated under reflux for a further 15 min. The solution was cooled to approx. 10° C. by means of an ice-bath, and sodium borohydride (30 g) was added portionwise with stirring, maintaining the temperature below 20° C. The solution was stirred for 2 h. at room temperature, then water (3 l) was added to precipitate the product, which was filtered off and washed with water (3×1 l). A solution of the crude solid in dichloromethane (1 l) was washed neutral with water (2×1 l), dried (Na$_2$SO$_4$) and evaporated to dryness. Crystallisation of the resulting white solid from acetone afforded (2α,3α,5α,16β,17β)-2,3-epoxy-16-(1-pyrrolidinyl)-androstan-17-ol (85.2 g), m.p. 156°-160° C.; [α]$_D^{20}$+33.6° (c 1.05 in CHCl$_3$)

EXAMPLE 2

(2α,3α,5α,16β,17β)-2,3-epoxy-16-(1-piperidinyl)-androstan-17-ol

A solution of (2α,3α,5α,16α,17β)-2,3,16,17-diepoxyandrostan-17-ol acetate (450 g) in piperidine (1.8 l) and water (200 ml) was heated under reflux for 1 h., then distilled to remove part of the piperidine (ca. 1.25 l). The remainder was cooled and brine was added to precipitate the product as a gum, which was washed with water several times, by decantation. The gum was dissolved in dichloromethane and the solution was washed with water, dried (MgSO$_4$), and evaporated to give the intermediate 17-ketone (442 g), which was dissolved in methanol (4.42 l) and reduced with sodium borohydride, as described above to give (2α,3α,5α,16α,17β)-2,3-epoxy-16-(1-piperidinyl)-androstan-17-ol, as a colourless solid. The product could be used in the next stage, without further purification, but a pure sample (from diethyl ether) had m.p. 153°-165° C., [α]$_D^{20}$=+28.4° (c 0.99 in CHCl$_3$).

EXAMPLE 3

(2β,3α,5α,16α,17β)-2-(4-morpholinyl)-16-(1-pyrrolidinyl)-androstane-3,17-diol

Water (50 ml) was added to a solution of (2α,3α,5α,16β,17β)2,3-epoxy-16-(1-pyrrolidinyl)-androstan-17-ol (85.2 g) in morpholine (500 ml) and the reaction mixture was heated at reflux temperature for 3 d. Evaporation of the reaction mixture gave a crude product, which was crystallised from acetone. Recrystallisation from methanol gave pure (2β,3α,5α,16β,17β)-2(4-morpholinyl)-16-(1-pyrrolidinyl)-androstane-3,17-diol (71.2 g), m.p. 212°-219° C.; [α]$_D^{20}$=+87.9° (c 1.02 in CHCl$_3$).

EXAMPLE 4

(2β,3α,5α,16β,17β)-2-(4-morpholinyl)-16-(1-piperidinyl)-androstane-3,17-diol

In a manner similar to that described above, (2β,3α,5α,16β,17β)-2-(4-morpholinyl)-16-(1-piperidinyl)-androstane-3,17-diol was prepared and crystallised from dichloromethane-acetone; m.p. 222°–229° C.; $[\alpha]_D^{20} = +81.1°$ (c 1.23 in CHCl$_3$).

EXAMPLE 5

(2β,3α,5α,16β,17β)-2-(4-morpholinyl)-16-(1pyrrolidinyl)-androstane-3,17-diol diacetate Acetyl chloride (10.0 ml) was added to a stirred suspension of (2β,3α,5α,16β,17β)-2-(4-morpholinyl)-16-(1pyrrolidinyl)-androstane-3,17-diol (10.0 g) in dichloromethane (100 ml). After 24 h. at room temperature, saturated potassium bicarbonate solution (approx. 20 ml) was added to give pH>7; the dichloromethane layer was separated, washed with water (3×150 ml), dried (Na$_2$SO$_4$) and evaporated to dryness to afford (2β,3α,5α,16β,17β)-2-(4-morpholinyl)-16-(1pyrrolidinyl)-androstane-3,17-diol diacetate as an off-white froth (7.78 g), $[\alpha]_D^{20} = +11.4°$ (c 0.57 in CHCl$_3$)

In a way similar to Example 1, 3 and this example the corresponding 16-(4'-methyl-piperazin-1-yl) compound was prepared, $[\alpha]_D^{20} = +34.3°$ (c =1,08 in CHCl$_3$).

EXAMPLE 6

(2β,3α,5α,16β,17β)-2-(4-morpholinyl)-16-(1-piperidinyl)-androstane-3,17-diol diacetate In a manner similar to that described above, (2α,3α,5α,16β,17β)-2-(4-morpholinyl)-16-(1pyrrolidinyl)-androstane-3,17-diol diacetate was prepared and crystallised from acetone; m.p. 119°–128° C.; $[\alpha]_D^{20} = +30.3°$ (c 0.72 in CHCl$_3$).

EXAMPLE 7

(2β,3α,5α,16β,17β)-2-(4-morpholinyl)-16-(1pyrrolidinyl)-androstane-3,17-diol 17-acetate Acetyl chloride (9.63 ml) was added to a solution of (2β,3α,5α,16β,17β)-2-(4-morpholinyl)-16-(1pyrrolidinyl)-androstane-3,17-diol (53.5 g) in dichloromethane (2.14 l) and the reaction was set aside at room temperature for 18 h. The solvent was removed under reduced pressure, and the residue was taken up in dichloromethane (500 ml). The solution was washed with 5% sodium carbonate solution (500 ml) and water (2×500 ml), dried (Na$_2$SO$_4$), and evaporated to dryness to yield a gum (59.9 g), which was chromatographed on alumina (Fluka type 5016A) (50 g). Crystallisation of the material, from pure fractions, from diethyl ether-n-hexane afforded (2β,3α,5α,16β,17β)-2-(4-morpholinyl)-16-(1-pyrrolidinyl)-androstane-3,17-diol 17-acetate (28.0 g), m.p. 149°–153° C. $[\alpha]_D^{20} = +54.0°$ (c 1.03 in CHCl$_3$).

EXAMPLE 8

(2β,3α,5α,16β,17β)-2-(4-morpholinyl)-16-(1piperidinyl)-androstane-3,17-diol 17-acetate In a similar manner, (2β,3α,5α,16β,17β)-2-(4-morpholinyl)-16-(1pyrrolidinyl)-androstane-3,17-diol 17-acetate was prepared, and crystallised from dichloromethane-n-hexane; m.p. 177°–184° C.; $[\alpha]_D^{20} = +77.5°$ (c 0.68 in CHCl$_3$).

EXAMPLE 9

(2β,3α,5α,16β,17β)-2-(4-morpholinyl)-16-(1pyrrolidinyl)-androstane-3,17-diol 3-acetate A solution of (2β,3α,5α,16β,17β)-2-(4-morpholinyl)-16-(1pyrrolidinyl)-androstane-3,17-diol diacetate (6.0 g) in methanol (70 ml) was set aside at room temperature for 20 h., during which time the product partially crystallised. Water (150 ml) was added to precipitate the product as a yellow solid, which was filtered off and dried. The crude solid was recrystallised from ethanol (110 ml) to give (2β,3α,5α,16β,17β)-2-(4-morpholinyl)-16-(1pyrrolidinyl)-androstane-3,17-diol 3-acetate (4.70 g), m.p. 112°–118° C.; $[\alpha]_D^{20} = +33.1°$ (c 0.97 in CHCl$_3$)

EXAMPLE 10

(2β,3α,5α,16β,17β)-2-(4-morpholinyl)-16-(1-piperidinyl)-androstane-3,17-diol 3-acetate In a similar manner, the title compound was prepared from (2β,3α,5α,16β,17β)-2-(4-morpholinyl)-16-(1-piperidinyl)-androstane-3,17-diol diacetate and crystallised from aqueous methanol; m.p. 148°–152° C.; $[\alpha]_D^{20} = +32.7°$ (c 1.37 in CHCl$_3$).

EXAMPLE 11

(2β,3α,5α,16β,17β)-2-(4-morpholinyl)-16-(1pyrrolidinyl)-androstane-3,17-diol 3-acetate 17-butanoate Butanoyl chloride (2.2 ml) was added to a solution of (2β,3α,5α,16β,17β)-2-(4-morpholinyl)-16-(1pyrrolidinyl)-androstane-3,17-diol 3-acetate (4.3 g) in dichloromethane (43 ml) and the solution was set aside at room temperature for 40 h. The solution was evaporated to dryness under reduced pressure to give a gum, which was taken up in dichloromethane (40 ml). The solution was washed with 5% sodium carbonate solution (15 ml) and water (3×100 ml), dried (Na$_2$SO$_4$) and evaporated to dryness to give (2β,3α,5α,16β,17β)-2-(4-morpholinyl)-16-(1pyrrolidinyl)-androstane-3,17-diol 3-acetate 17-butanoate as a froth (4.2 g), $[\alpha]_D^{20} = +6.5°$ (c 1.19 in CHCl$_3$).

EXAMPLE 2

(2β,3α,5α,16β,17β)-2-(4-morpholinyl)-16-(1piperidinyl)-androstane-3,17-diol 3-acetate 17-butanoate In a similar manner, the title compound was prepared as a froth from (2β,3α,5α,16β,17β)-2-(4-morpholinyl)-16-(1-piperidinyl)-androstane-3,17-diol 3-acetate; $[\alpha]_D^{20} = +25.7°$ =(c 0.93 in CHCl$_3$).

EXAMPLE 13

(2β,3α,5α,16β,17β)-2-(4-morpholinyl)-16-(1piperidinyl)-androstane-3,17-diol 3-acetate 17propanoate In a similar manner, the title compound was prepared as a froth using propanoyl chloride; $[\alpha]_D^{20} = +26.9°$ (c 0.93 in CHCl$_3$).

EXAMPLE 14

1-[(2β,3α,5α,16β,17β)-3,17-bis(acetyloxy)-2-(4-morpholinyl)-androstan-16yl]-1-methylpyrrolidinium bromide Bromomethane (3.75 g) was added to a solution of (2β,3α,5α,16β,17β)-2-(4-morpholinyl)-16-(1-pyrrolidinyl)-androstane-3,17-diol diacetate (2.5 g) in dichloromethane (50 ml). The solution was sealed in a pressure bottle and set aside at room temperature for 20 h. The solvent was removed under reduced pressure with the minimum of heating to afford an off-white solid, which was dissolved in acetone (15 ml). Diethyl ether (100 ml) was added to precipitate 1-[(2β,3α,5α,16β,17β)-3,17-bis(acetyloxy)-2-(4-morpholinyl)-androstan-16-yl]-1-methylpyrrolidinium bromide (1.97 g), m.p. 184°–191° C.; $[\alpha]_D^{20} = -17.1° = $(c 0.93 in CHCl$_3$)

EXAMPLE 15

1-[(2β,3α,5α,16β,17β)-3,17-bis(acetyloxy)-2-(4-morpholinyl)-androstan-16yl]-1-methylpiperidinium bromide In a similar manner, 1-[(2β,3α,5α,16β,17β)-3,17-bis-(acetyloxy)-2-(4-morpholinyl)-androstan-16-yl]-1-methylpiperidinium bromide was prepared and crystallised from dichloromethane-acetone; m.p. 231°–234° C.; $[\alpha]_D^{20} = -17.9°$ (c 1.06 in CHCl$_3$).

EXAMPLE 16

1-[(2β,3α,5α,16β,17β)-17-acetyloxy-3-hydroxy-2-(4-morpholinyl)-androstan-16-yl]-1-methylpyrrolidinium bromide In a similar manner, the title compound was prepared from (2β,3α,5α,16β,17β)-2-(4-morpholinyl)-16-(1-pyrrolidinyl)-androstan-3,17diol 17- acetate and crystallised from acetone-diethyl ether; m.p. 193°–199° C. (decomp.), $[\alpha]_D^{20} = +12.2°$ (c 1.12 in CHCl$_3$).

EXAMPLE 17

1-[(2β,3α,5α,16β,17β)-17acetyloxy-3-hydroxy-2-(4-morpholinyl)-androstan-16-yl]-1-methylpiperidinium bromide In a similar manner, the title compound was prepared from (2β,3α,5α,16β,17β)-2-(4-morpholinyl)-16-(1-piperidinyl)-androstane-3,17-diol 17-acetate and crystallised from dichloromethane-diethyl ether; m.p. 188°–195° C.; $[\alpha]^{D20} = +10.9°$ (c 1.26 in CHCl$_3$).

EXAMPLE 18

1-[(2β,3α,5α,16β,17β)-3-(acetyloxy)-17-(1-oxobutoxy)-2-(4-morpholinyl)-androstan-16-yl]-1-methylpyrrolidinium bromide In a similar manner, the title compound was prepared from (2β,3α,5α,16β,17β)-2-(4-morpholinyl)-16-(1-pyrrolidinyl)-androstane-3,17-diol 3-acetate 17butanoate and crystallised from ethanoldichloromethane-diethyl ether; m.p. 209°–214° C. (decomp.); $[\alpha]_D^{20} = -16.2°$ (c 1.02 in CHCl$_3$).

EXAMPLE 19

1-[(2β,3α,5α,16β,17β)-3-(acetyloxy)-17-(1-oxobutoxy)-2-(4-morpholinyl)-androstan-16-yl]1-methyl-piperidinium bromide In a similar manner, the title compound was prepared from (2β,3α,5α,16β,17β)-2-(4-morpholinyl)-16-(1-piperidinyl)-androstane-3,17-diol 3-acetate 17-butanoate and crystallised from dichloromethane-acetone-diethyl ether; m.p. 208°–214° C. (decomp.) $[\alpha]_D^{20} = -15.1°$ (c 0.93 in CHCl$_3$).

EXAMPLE 20

1-[(2β,3α,5α,16β,17β)-3-(acetyloxy)-17-(1-oxopropoxy)-2-(2-morpholinyl)-androstan-16-yl]-1-methylpiperidinium bromide.

In a similar manner, the title compound was prepared from (2β,3α,5α,16β,17β)-2-(4-morpholinyl)-16-(1-piperidinyl)-androstane-3,17-diol 3-acetate 17-propanoate and crystallised from dichloromethaneacetone, m.p. 230°–235° C. (decomp.); $[\alpha]_D^{20} = -16.8°$ (c 1.03 in CHCl$_3$)

EXAMPLE 21

1-[(2β,3α,5α,16β,17β)-3,17-dihydroxy-2-(4-morpholinyl)-androstan-16-yl]-1-methylpiperidinium bromide.

In a similar manner, the title compound was prepared from (2β,3α,5α,16β,17β)-2-(4-morpholinyl)-16-(1-piperidinyl)-androstane-3,17-diol in a mixture of ethanol (10 vols.) and dichloromethane (10 vols.) at room temperature for 48 h. and crystallised from dichloromethane-acetone; m.p. >250° C. (decomp.); $[\alpha D^{20} = +35.8°$ (c 0.88 in CHCl$_3$).

EXAMPLE 22

1-[(2β,3α,5α,16β,17β)-3-(acetyloxy)-17-hydroxy-2(4-morpholinyl)-androstan-16-yl]-1methylpiperidinium bromide In a similar manner, the title compound was prepared from (2β,3α,5α,16β,17β)-2-(4-morpholinyl)-16-(1-piperidinyl)-androstane-3,17-diol 3-acetate and crystallised from dichloromethane-ether; m.p. >250° C. (decomp.); $[\alpha]_D^{20} = +3.6°$ (c 0.86 in CHCl$_3$).

EXAMPLE 23

1-[(2β,3α,5α,16β,17β)-17-acetyloxy-3-hydroxy-2-(4-morpholinyl)-androstan-16-yl]-1(2-propenyl)pyrrolidinium bromide 2-propenyl bromide (1.95 ml) was added to a solution of (2β,3α,5α,16β,17β)-2-(4-morpholinyl)-16(1-pyrrolidinyl)-androstane-3,17-diol 17-acetate (1.35 g) in dichloromethane (27 ml) and the solution was sealed in a pressure bottle at room temperature for 22 h. The solvent was removed under reduced pressure with the minimum of heating and the crude solid (1.59 g) was chromatographed on alumina (Fluka type 5016A). The pure fractions were combined, taken up in dichloromethane (15 ml) and diethyl ether (100 ml) was added to precipitate pure 1-[(2β,3α,5α,16β,17β)-17-acetyloxy-3-hydroxy-2-(4-morpholinyl)-androstan-16-yl]-1-(2propenyl)-pyrrolidinium bromide (1.14 g), m.p. 161°–169° C.; $[\alpha]_D^{20} = +18.7°$ (c 1.03 in CHCl$_3$).

EXAMPLE 24

1-[(2β,3α,5α,16β,17β)-3,17-bis(acetyloxy)-2-(4-morpholinyl)-androstan-16-yl]-1-(2-propenyl)pyrrolidinium bromide In a similar manner, the title compound was prepared from (2β,3α,5α,16β,17β)-2-(4-morpholinyl)-16-(1pyrrolidinyl)-androstane-3,17-diol diacetate and crystallised from acetone-diethyl ether; m.p. 179°–186° C.; $[\alpha]_D^{20} = -9.6°$ (c 0.86 in CHCl$_3$).

EXAMPLE 25

1-[(2β,3α,5α,16β,17β)-3,17-bis(acetyloxy)-2-(4-morpholinyl)-androstan-16-yl]-1-(2propenyl)piperidium bromide In a similar manner, the title compound was prepared from (2β,3α,5α,16β,17β)-2-(4-morpholinyl)-16-(1-piperidinyl)-androstane-3,17-diol diacetate and crystallised from dichloromethane-diethyl ether; m.p. 164°–168° C.; $[\alpha]_D^{20} = -17.0°$ (c 0.64 in CHCl$_3$).

EXAMPLE 26

1-[(2β,3α,5α,16β,17β)-3-acetyloxy)-17-(1-oxobutoxy)-2-(4-morpholinyl)-androstan-16-yl]1-(2-propenyl)-piperidinium bromide In a similar manner, the title compound was prepared from (2β,3α,5α,16β,17β)-2-(4-morpholinyl)-16-(1-piperidinyl)-androstane-3,17-diol 3-acetate 17-butanoate as a non-crystalline solid, m.p. 152°–156° C.; $[\alpha]_D^{20} = -12.2°$ (c 1.20 in CHCl$_3$).

EXAMPLE 27

1-[(2β,3α,5α,16β,17β)-3-acetyloxy)-17-(1-oxopropoxy)-2-(4-morpholinyl)-androstan-16-yl]1-(2-propenyl)-piperidinium bromide In a similar manner, the title compound was prepared from (2β,3α,5α,16β,17β)-2-(4-morpholinyl)-16-(1-piperidinyl)-androstane-3,17-diol 3-acetate 17-propanoate and crystallised from acetone-diethyl ether; m.p. 180°–189° C. (decomp.), $[\alpha]_D^{20} = -14.2°$ (c 1.27 in CHCl$_3$).

EXAMPLE 28

1-(2β,3α,5α,16β,17β)-3.17-dihydroxy-2-(4-morpholinyl)-androstan-16-yl]1-(2-propenyl) pyrrolidinium bromide In a similar manner, the title compound was prepared from (2β,3α,5α,16β,17β)-2-(4-morpholinyl)-16-(1-pyrrolidinyl)-androstane-3,17-diol and crystallised from methanol-acetone; m.p. 208°–215° C. (decomp.); $[\alpha]_D^{20} = +42.8°$ (c 0.79 in CHCl$_3$).

EXAMPLE 29

1-[(2β,3α,5α,16β,17β)-3,17-bis(acetyloxy)-2-(4-morpholinyl)-androstan-16-yl]1-(2-propynyl)pyrrolidinium bromide 1-[(2β,3α,5α,16β,17β)-3,17-bis(acetyloxy)-2-(4-morpholinyl)-androstan-16-yl]-1-(2-propynyl)pyrrolidinium bromide was prepared in a similar way, using 3-bromo-1-propyne and crystallised from dichloromethane-diethyl ether; m.p. 151°–154° C.; $[\alpha]_D^{20} = -9.2°$ (c 1.01 in CHCl$_3$).

EXAMPLE 30

1-(2β,3α,5α,16β,17β)-3-(acetyloxy)-17-hydroxy-2-(4-morpholinyl)-androstan-16-yl]1-(2-propenyl)pyrrolidinium bromide m.p. 218°–220° C. (decomp.), $[\alpha]_D^{20} = +10.6°$ (c=1.04 in CHCl$_3$).

In a similar way the title compound was prepared from (2β,3α,5α,16β,17β)-2-(4-morpholinyl)-16-(1-pyrrolidinyl)-androstane-3,17-diol 3-acetate.

EXAMPLE 31

1-[(2β,3α,5α,16β,17β)-3,17-bis(acetyloxy)-2-(4-morpholinyl)-androstan-16-yl]-1ethylpiperidinium bromide Bromoethane (20 ml) was added to a solution of (2β,3α,5α,16β,17β)-2-(4-morpholinyl)-16(1-piperidinyl)-androstane-3,17-diol diacetate (2.5 g.) in acetonitrile (25 ml) and the mixture was heated in an autoclave at 95° C. for 16 h. The resulting brown solution was evaporated to dryness under reduced pressure to give a gum (2.85 g), which was dissolved in the minimum of dichloromethane (15 ml). Diethyl ether (70 ml) was added to precipitate the crude product (2.12 g), which was purified by chromatography on alumina (Fluka, type 5016A) (80 g). Crystallisation of the eluted material from dichloromethane-diethyl ether gave 1-[(2β,3α,5α,16β,17β)-3,17-bis(acetyloxy)-2-(4-morpholinyl)-androstan-16-yl]-1-ethylpiperidinium bromide (1.28 g), m.p. 193°–196° C. (decomp.), $[\alpha]_D^{20} = -18.0°$ (c 1.1 in CHCl$_3$).

EXAMPLE 32

1-[(2β,3α,5α,16β,17β)-3-acetyloxy)-17-(1-oxobutoxy)-2-4-morpholinyl)-androstan-16-yl]-1-ethylpiperidinium bromide In a similar manner, the title compound was prepared from (2β,3α,5α,16β,17β)-2-(4-morpholinyl)-16-(1-piperidinyl)-androstane-3,17-diol 3-acetate 17-butanoate and precipitated from a solution of dichloromethane by the addition of diethyl ether, to give a non-crystalline solid, m.p. 161°–168° C.; $[\beta]_D^{20} = -15.5°$ (c 0.95 in CHCl$_3$).

EXAMPLE 33

1-[(2β,3α,5β,16α,17β)-3,17-bis(acetyloxy)-2-(4-morpholinyl)-androstan-16-yl]-1-(cyclopropylmethyl)pyrrolidinium bromide Cyclopropylmethyl bromide (1.0 ml) was added to a solution of (2β,3α,5α,16β,17β)-2-(4-morpholinyl)-16-(1-pyrrolidinyl)-androstane-3,17-diol diacetate (2.0 g) in acetonitrile (20 ml) and the solution was heated under reflux for 14 d. Evaporation of the reaction mixture to dryness under reduced pressure gave a pale brown solid (2.30 g), which was crystallised from dichloromethanediethyl ether to remove most of the unreacted starting material. Further purification, by chromatography on alumina as described above, gave material, which was dissolved in dichloro-methane and precipitated from the solution with diethyl ether to give 1-[(2β,3α,5α,16β,17β)-3,17-bis(acetyloxy)-2-(4-morpholinyl)-androstan-16-yl]-1-(cyclopropylmethyl) pyrrolidinium bromide, m.p. decomposes above 175° C.; $[\alpha]_D^{20} = -11.6°$ (c 0.66 in CHCl$_3$).

EXAMPLE 34

1-[(2β,3α,5α,16β,17β)-3,17-(acetyloxy)-3-hydroxy-2-(4-morpholinyl)-androstan-16-yl]-1-methylpiperidinium bromide A solution of 1-(2β,3α,5α,16β,17β)-3,17-bis-(acetyloxy)-2-(4-morpholinyl)-androstan-16-yl]-1-methylpiperidinium bromide (10.5 g) in water (300 ml) was stirred at room temperature for 14 d., then evaporated to dryness under reduced pressure. The final traces of water were removed by dissolving the residue in toluene (300 ml) and evaporating the solution to dryness. This procedure was repeated, then the crude product (9.8 g) was purified by chromatography on alumina (Fluka type 5016A) (300 g) to obtain, on crystallisation from dichloromethane-diethyl ether, the title compound (8.85 g), m.p. and $[\alpha]_D^{20}$ = as described earlier.

EXAMPLE 35

Prepared in a similar manner, by aqueous hydrolysis of the appropriate diester quaternary ammonium bromides were:

1-[(2β,3α,5α,16β,17β)-17-acetyloxy-3-hydroxy-2-(4-morpholinyl)-androstan-16-yl]-1-methylpyrrolidinium bromide, m.p. and $[\alpha]_D^{20}$ = as described earlier (from diacetate).

1-[(2β,3α,5α,16β,17β)-17-acetyloxy-3-hydroxy-2-(4-morpholinyl)-androstan-16-yl]-1-(2-propenyl) pyrrolidinium bromide, m.p. and [α]$_D^{20}$=as described earlier (from diacetate).

1-[(2β,3α,5α,16β,17β)-3-hydroxy-2-(4-morpholinyl)-17-(1-oxobutoxy)-androstan-16-yl]-1-methylpyrrolidinium bromide, m.p. 174°–179° C.; [α]$_D^{20}$= +13.6° (c 0.96 in CHCl$_3$) (from 3-acetate 17-butanoate).

1-[(2β,3α,5α,16β,17β)-3-hydroxy-2-(4-morpholinyl)-17-(1-oxobutoxy)-androstan-16-yl]-1-(2-propenyl)-piperidinium bromide, m.p. 151°–153° C.; [α]$_D^{20}$= +12.9° (c 1.27 in CHCl$_3$) (from 3-acetate 17-butanoate).

1-[(2β,3α,5α,16β,17β)-3-hydroxy-2-(4-morpholinyl)-17-(1-oxopropoxy)-androstan-16-yl]-1-methylpiperidinium bromide, m.p. 204°–219° C. (decomp.); [α]$_D^{20}$= +12.1° (c 1.03 in CHCl$_3$) (from 3-acetate 17-propanoate).

1-[(2β,3α,5α,16β,17β)-3-hydroxy-2-(4-morpholinyl)-17-(1-oxopropoxy)-androstan-16-yl]-1-(2-propenyl)-piperidinium bromide, [α]$_D^{20}$= +11.7° (c 1.18 in CHCl$_3$) (amorphous solid) (from 3-acetate 17-propanoate).

EXAMPLE 36

1-[(2β,3α,5α,16β,17β)-2-(4-morpholinyl)-3,17-bis(1-oxopropoxy)-androstan-16-yl]-1-methyl-piperidinium bromide Propanoyl chloride (5.24 ml) was added to a solution of 1-[(2β,3α,5α,16β,17β)-3-hydroxy-2(4-morpholinyl)-17-(1-oxopropoxy)-androstan-16-yl]-1-methyl-piperidinium bromide (2.62 g) in dichloro-methane (33 ml) and the solution was set aside at room temperature for 20 h. The solution was evaporated to dryness under reduced pressure to give a gum, which was taken up in dichloromethane (15 ml) and purified by chromatography on alumina (Fluka type 5016A) (62 g) to give 1-[(2β,3α,5α,16β,17β)-2-(4-morpholinyl)-3,17-bis(1-oxopropoxy)-androstan-16-yl]-1-methylpiperidinium bromide as a non-crystalline solid (1.99 g), [α]$_D^{20}$= −16.7° (c 1.09 in CHCl$_3$).

EXAMPLE 37

1-[(2β,3α,5α,16β,17β)-2-(4-morpholinyl)-3,17-bis (1-oxopropoxy)-androstan-16-yl]-1-(2-propenyl)-piperidinium bromide was prepared in a similar manner by esterification of 1-[(2β,3α,5α,16β,17β)-3-hydroxy-2-(4-morpholinyl)-17-(1-oxopropoxy)-androstan-16-yl]-1-(2propenyl)piperidinium bromide and crystallised from acetone-diethyl ether; m.p. 145°–148° C.; [α]$_D^{20}$= −14.3° (c 0.95 in CHCl$_3$).

EXAMPLE 38

1-[(2β,3α,5α,16β,17β)-b 17-acetyloxy-3-(3-carboxy-1-oxopropoxy)-2-(4-morpholinyl)-androstan-16-yl]-1-methylpyrrolidinium bromide Succinic anhydride (0.24 g) was added to a solution of 1-[(2β,3α,5α,16β,17β)-17-acetyloxy-3-hydroxy-2-(4-morpholinyl)-androstan-16-yl]-1-methylpyrrolidinium bromide (0.89 g) in dichloromethane (25 ml) and the mixture was heated under reflux for 11 h. When the solution had cooled to room temperature, diethyl ether (100 ml) was added to precipitate the product, which was crystallised from acetone-diethyl ether; m.p. 159°–168° C.; [α]$_D^{20}$= −11.2° (c 0.96 in CHCl$_3$).

EXAMPLE 39

1-[(2β,3α,5α,16β,17β)-17-acetyloxy-3-(3-carboxy-1-oxopropoxy)-2-(4-morpholinyl)-androstan-16-yl]-1-methylpiperidinium bromide was prepared in a similar manner from 1-(2β,3α,5α,16β,17β)-17-acetyloxy-3-hydroxy-2-(4-morpholinyl)-androstan-16-yl]-1-methylpiperidinium bromide and crystallised from dichloromethane-diethyl ether; m.p. 163°–170° C.; [α]$_D^{20}$= −14.5° (c 1.18 in CHCl$_3$).

EXAMPLE 40

In a way similar to Example 14 the 16-(4'-methylpiperazinyl) compound obtained in Example 5 was converted into the corresponding 16-(4',4'-dimethylpiperazinyl)-bromide, m.p. 236°–242° C. (decomp.); [α]$_D^{20}$= +26.7° (c =1.2 in CHCl$_3$).

EXAMPLE 41

The compounds obtained in Examples 15 and 33 are 5-times more potent than the corresponding 16β-morpholino compounds. The potency was tested by measuring the amount of compound necessary for obtaining a 50% reduction of the muscle tension in the Tibialis muscle in the cat.

We claim:
1. Compounds having the formula:

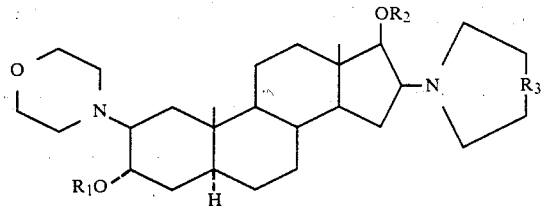

wherein R$_1$ is H or an optionally substituted acyl group having 1–12 carbon atoms, R$_2$ is H or an acyl group having 1–12 carbon atoms and R$_3$ is C, N—CH$_3$ or a direct bond, and mono- or bisquaternary ammonium compounds thereof and acid addition salts of the non- or mono-quaternary ammonium compounds.

2. Compounds according to claim 1, wherein R$_1$ is H.

3. Compounds according to claim 1, wherein the compounds are 16β-monoquaternary ammonium compounds.

4. Compounds according to claim 1, wherein R$_2$ is a saturated acyl group having 1–6 carbon atoms.

5. Compounds according to claim 1, wherein R$_3$ is C or a direct bond.

6. Compositions having neuromuscular blocking activity comprising an aqueous solution of at least one of the compounds claimed in claim 1 in a pharmaceutically effective amount.

* * * * *